United States Patent [19]

Gilbertson

[11] Patent Number: 5,541,289
[45] Date of Patent: Jul. 30, 1996

[54] PHOSPHINE CONTAINING AMINO ACIDS AND PEPTIDES AND METHODS OF PREPARING AND USING SAME

[75] Inventor: Scott R. Gilbertson, St. Louis, Mo.

[73] Assignee: Washington University, St. Louis, Mo.

[21] Appl. No.: 220,245

[22] Filed: Mar. 30, 1994

[51] Int. Cl.$^6$ .............................. B01J 31/24; C07F 9/50; C07K 1/113; C07K 7/08

[52] U.S. Cl. .................... 530/327; 502/159; 530/345; 530/334; 530/336; 548/412; 564/15; 585/275

[58] Field of Search .................... 548/412; 564/15; 530/333, 334, 336, 338, 340, 345, 327, 402, 403; 514/7; 424/1.69, 1.77; 534/14; 502/159; 585/275, 276, 277; 208/136, 137, 138

[56] References Cited

U.S. PATENT DOCUMENTS

| | | | |
|---|---|---|---|
| 4,917,879 | 4/1990 | Deutsch et al. | 534/14 |
| 5,061,641 | 10/1991 | Shochat et al. | 530/403 |
| 5,112,594 | 5/1992 | Woulfe et al. | 206/569 |
| 5,112,595 | 5/1992 | Woulfe et al. | 534/14 |

FOREIGN PATENT DOCUMENTS 0311352  4/1989  European Pat. Off. .
0386873  9/1990  European Pat. Off. .
WO91/03262  3/1991  WIPO .

OTHER PUBLICATIONS

Grant, ed., Hackh's Chemical Dictionary, 4th ed., published 1969 by McGraw–Hill Book Co. (NY), p. 36.

Z. Naturforsch, vol. 38b, issued 1983, Trampisch et al, "Diphenylphosphino–2–aminosaureester als Liganden . . . ", pp. 365–369.

Recent Advances in Technetium Chemistry: Bridging Inorganic Chemistry and Nuclear Medicine, *Comments Inorg. Chem.* 3:83–103 (1984).

Lever, S., et al., Synthesis of a Novel Bifunctional Chelate Designed for Labeling Proteins with Technetium, *Tetrahedron Letters* 29:3219–3222 (1988).

*Primary Examiner*—Jeffrey E. Russel
*Attorney, Agent, or Firm*—Howell & Haferkamp, L.C.

[57] ABSTRACT

A method for incorporating novel phosphine containing amino acids into peptide sequences is provided. The resulting phosphine-containing peptides can be used to bind a transition metal between two phosphine moieties presented on an amino acid in a peptide. The resulting phosphine-containing peptide metal complex is useful as a stereoselective catalyst of a chemical reaction or as a means for delivering a metal selectively to a target tissue or organ for medical uses.

21 Claims, 10 Drawing Sheets

PHOSPHINE CONTAINING AMINO ACIDS AND PEPTIDES AND METHODS OF PREPARING AND USING SAME

BACKGROUND OF THE INVENTION

1. Field of the Invention

This invention relates in general to peptide-based metal binding ligands, and more particularly to phosphine-containing peptide ligands that provide an asymmetric peptide ligand capable of binding transition metals.

2. Description of Background Art

It has long been known that the phosphine moiety is highly useful as a ligand for a wide variety of catalytically active transition metals. Phosphine metal complexes are known to be used in commercially useful chemical reactions, such as hydroformylation, the hydrogenation of olefins, catalytic allylic alkylation, and the hydrosilation, hydrocyanation, and hydrovinylation of olefins. Phosphine ligands have also been used extensively to bind transition metals for medical uses, such as in the preparation of medical imaging agents.

It has also been a goal of the chemical and pharmaceutical industries to be able to influence the stereospecificity of the product of chemical reactions. In fact, many of the chemical reactions described above have been run using chiral phosphine ligands in an attempt to induce asymmetry in the reaction. Unfortunately, in most cases the enantiomeric excess obtained has been too low for the process to be useful commercially. There has also been an increasing awareness of the advantages of administering only the biologically active enantiomers of pharmaceutical compounds and the use of asymmetric catalysts, using chiral ligands, in the manufacture of such compounds. The technical aspects of these objectives are the subject of extensive research efforts. For example, one can envision using an asymmetric hydroformylation catalyst in the hydroformylation of styrene analogs for the asymmetric synthesis of the class of anti-inflammatory drugs, including Naproxen and analogs thereof. Hydrocarbonylation is a potential route to the production of chiral lactones and lactams, two biologically important functional groups. The chiral phosphine ligands that have been developed to date are, however, typically substrate specific and not suitable for general use. That is, a system that works in an asymmetric fashion with one molecule may not work in the same way with a different molecule.

Typical catalytic phosphine complexes consist of a diphosphine ligand bonded to a chiral hydrocarbon backbone. This places the chirality on one side of the catalytic metal while the actual catalysis must take place at the coordination sites at the opposite side of the metal. This means that in most cases the transfer of chirality from the ligand to the product determining step (the transition state) is not efficient. It is believed that if a chiral ligand could be prepared that is large enough to reach the opposite face of the metal, the ligand would be able to strongly influence the asymmetric environment of the face of the metal where the reaction is taking place and consequently the synthesis of the product. Conventional phosphine-metal chiral ligands having the diphosphine ligand bonded to a chiral hydrocarbon backbone are typically small molecules. To develop a hydrocarbon based chiral ligand that is large enough, or that has a structure capable of affecting the environment at the face of the metal where the reaction takes place, one would encounter great difficulty.

There are a number of types of biological macromolecules that are capable of forming unique, stable three-dimensional structures. It would be desirable to use these structures to control the reactivity of various transition metals. Peptides are large asymmetric molecules that can fold into regular three-dimensional asymmetric secondary structures. It is believed that the highly asymmetric environment of a peptide could be used as a platform for a catalytic metal. Attaching a metal to this large asymmetric ligand could permit the systematic control of the asymmetric environment at the catalytically active face of the metal. If one could provide a means for attaching a metal to a peptide, the stable secondary structure of the peptide would permit the ligand to more readily influence the asymmetric environment at the side of the metal where the reaction takes place. Moreover, peptides often have useful characteristics that could be exploited for various medical applications. For example, a peptide has a distinct solubility, lipophilicity, and bioavailability, and some peptides have selective affinity for particular biological tissues or organs. Moreover, by synthesizing a unique peptide by solid phase peptide synthesis, a peptide having a particular set of characteristics can be designed and synthesized.

In order to utilize the structural characteristics of peptides as a phosphine containing ligand, a method for the incorporation of phosphine into any peptide sequence must be provided. Heretofore, no such method has been developed and no phosphine amino acids or peptides containing phosphine containing amino acids have been reported.

SUMMARY OF THE INVENTION

The present invention is directed to a method for incorporating novel phosphine containing amino acids into peptide sequences to provide novel phosphine containing peptides. These peptides can be used to bind a transition metal between two phosphine moieties presented on an amino acid in a peptide or a mixture of peptides for use as a stereoselective catalyst for a chemical reaction or for delivery of a metal selectively to a target tissue or organ in an organism. According to the method, amino acids containing a phosphine moiety protected as the phosphine sulfide are prepared, incorporated into a peptide sequence to produce a peptide that has amino acids having the phosphine sulfide moiety, and the peptide is reacted with a reducing agent such as Raney nickel, to remove the sulfide group from the phosphine sulfide amino acids in the peptide to yield a peptide containing the phosphine moieties. The phosphine containing peptide can be reacted with a transition metal to bind the metal between two phosphine moieties that are sufficiently near enough to each other in the peptide to enable them to bind the metal therebetween. This phosphine peptide-metal complex can then be used as a catalyst to induce asymmetry into a chemical reaction or as a means for delivering the metal to a particular biological site by virtue of the physical and biological characteristics of the peptide.

The present invention is further directed to novel amino acids containing the phosphine moiety. The amino acids may present the phosphine moiety protected by a sulfide group. For the incorporation of a phosphine containing amino acid into a peptide, the phosphine group must be protected with the sulfide.

The present invention is also directed to novel peptides which include phosphine containing amino acids in their primary structure. Preferably, the phosphine amino acids are positioned spatially in a peptide or a mixture of peptides in a manner that permits the binding of a transition metal between the two phosphine moieties. Thus, a peptide sequence can be prepared containing at least two phosphine amino acids if the metal is to be bound to a single peptide sequence, or if a metal is to be bound between two peptide sequences, each sequence must contain at least one phosphine containing amino acid. The present invention is further directed to phosphine-containing peptide-metal complexes that can be utilized as a stereoselective catalyst for chemical reactions or as a metal delivery vehicle, such as for use as a medical imaging agent.

A still further aspect of the present invention is to provide a method for producing a chiral end product in a chemical reaction by using a phosphine-containing peptide-metal complex of this invention as the catalyst for such reaction.

Among the several advantages found to be achieved by the present invention include the provision of a method for introducing a metal-binding ligand into a peptide sequence; a method for introducing a phosphine-containing amino acid into a peptide that permits the use of conventional solid phase peptide synthesis methods; a method that can be used to prepare a phosphine-containing peptide having a selected primary or secondary structure; a phosphine-containing peptide that can be used as a catalyst for a chemical reaction when a catalytic transition metal is bound to the phosphine moieties; a phosphine-containing peptide that can be used to deliver a metal to a selected biological site in an organism; a chiral phosphine peptide-metal complex that can be used to influence the asymmetric environment of the face of the metal where a reaction takes place; a method for producing a chiral product using a phosphine-containing peptide as the catalyst; and the provision of methods for preparing novel phosphine containing amino acids and peptides containing such amino acids.

BRIEF DESCRIPTION OF THE DRAWING FIGURES

DETAILED DESCRIPTION OF THE PREFERRED EMBODIMENTS

Figure 1:
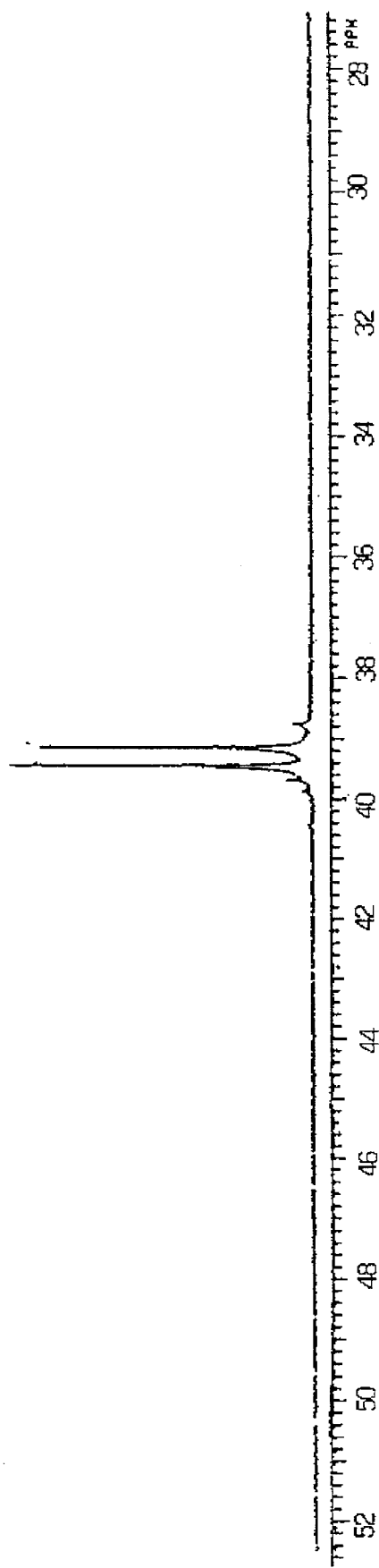
FIG. 1 shows the $^{31}$P NMR spectra for peptide sequence III (SEQ ID NO. 1) that contains the phosphine sulfide amino acids.
Figure 2:
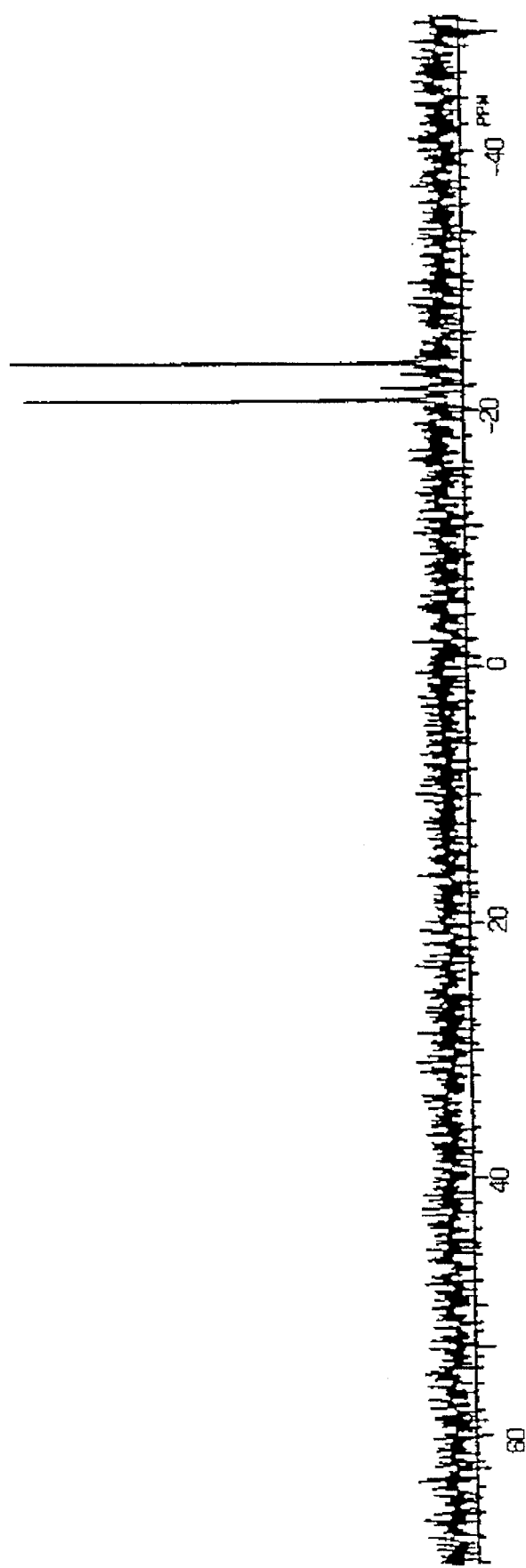
FIG. 2 shows the $^{31}$P NMR spectra for peptide sequence III (SEQ ID NO. 1) after reaction with Raney nickel to convert the phosphine sulfide groups to phosphines.

In accordance with the present invention, it has been discovered that novel phosphine containing amino acids can be prepared and can be incorporated into a peptide sequence to create a phosphine containing peptide that is capable of binding transition metals. The phosphine amino acid is synthesized as a phosphine sulfide which enables it to be utilized in conventional solid phase peptide synthesis to prepare a peptide containing the phosphine sulfide moieties. The phosphine moiety is regenerated in the peptide by reacting the phosphine sulfide containing peptide in a reductive desulfurization process using a suitable reductant such as Raney nickel or other metal species known to remove sulfur from a compound, or hydride reducing agents, i.e. lithium aluminum hydride and the like, to yield a phosphine containing peptide. As a result, phosphine containing peptides are provided that can be used to bind a catalytically active metal for use as a catalyst for stereoselective reactions, as well as to deliver such metal to a desired location in a biological fluid or system. The chirality of the phosphine containing peptide is based on the asymmetry of the peptide secondary structure which will influence the asymmetric environment of the bound transition metal. By using solid phase peptide synthesis, a variety of structurally different phosphine containing peptide ligands can be designed and synthesized.

The first step in the synthesis of the chiral phosphine containing peptide-metal complexes of this invention is the synthesis of the desired amino acid having the phosphine sulfide moiety bonded thereon. Derivatives of any amino acid onto which the phosphine sulfide moiety can be bonded to the side chain of the amino acid can be used in conjunction with the peptides of the present invention. This includes the twenty common amino acids of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine, as well as modified and unusual amino acids such as 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'diaminopimelic acid, 2,3 diaminopropionic acid, N-ethylglycine, N-ethylasparagine, hydroxylysine, allo-hydroxyproline, 3-hydroxyproline, 4-hydroxyproline, isodesmosine, alloisoleucine, N-methylglycine, N-methylisoleucine, N-methylvaline, norvaline, norleucine, ornithine and other compounds that have the basic amino acid structure. The phosphine moiety is ultimately introduced onto the side chain of the amino acid. This can be achieved by a variety of methods. In one method, an amino acid or a derivative of an amino acid is reacted with a selected phosphine under conditions that protect the features of the amino acid including the amine, the carboxyl and other moieties of the side chain to which the phosphine is not directly bound, and which permits incorporation of the phosphine onto the amino acid or amino acid derivative. In most instances, the amine and carboxyl groups of the amino acid will need to be protected, such as by the introduction of protecting groups onto the amino and/or carboxyl moieties, during the process by which the phosphine is introduced. Numerous means for protecting these groups are known and are routinely used by those skilled in the art. For example, a carboxyl group can be protected by conversion of the carboxyl to the oxazolidinone or by converting the carboxyl to an ester, reducing it to an alcohol and protecting it with a group such as t-butyldimethyl silyl ether. An amine group can be protected by conversion of the amine to a mesylate or protection by the addition of FMOC. It has been found that synthesis of a desired amino acid from an amino acid precursor or derivative to include the phosphine moiety is the preferred method of preparing an amino acid of this invention.

The phosphine moiety that is to be reacted with and ultimately bound to the amino acid has the general structure:

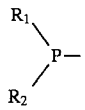

where $R_1$ and $R_2$ are the same or different and are selected from the group consisting of hydrogen, $C_1$-$C_5$ alkyl, such as methyl or ethyl, ether, such as methoxymethyl or methoxyethyl, $C_1$-$C_5$ alkylaryl, such as phenylmethyl or phenylpropyl, and $C_1$-$C_5$ dioxanylpropyl. Examples of suitable phosphine ligands include, but are not limited to, diphenylphosphine, diethylphosphine, methylbis (3-methoxypropyl) phosphine, and methylbis[2-[2-(1,3-dioxanyl] ethyl] phosphine. Each of these phosphine ligands are capable of binding Group VIA through Group IB transition metals. The resulting phosphine amino acid will have the general formula:

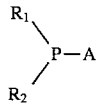

where A is the amino acid.

As described above, the phosphine amino acid ligand can be synthesized by derivation of known amino acids or prepared by complete synthesis of the required phosphine containing amino acid. So long as the resulting amino acid retains the amine and carboxylic acid functionalities, the phosphine amino acid is considered to be within the scope of this invention. It has also been found that once bound to the amino acid, the phosphine group can be protected by converting it to the phosphine sulfide. This renders the phosphine amino acid amenable to peptide synthesis by conventional solid phase procedures. Examples of the synthesis of phosphine amino acids in accordance with this invention are provided in the Examples which follow.

After the desired phosphine containing amino acid or amino acids have been selected and synthesized, the phosphine amino acids are incorporated into a peptide sequence. The phosphine containing amino acids of the present invention are amenable to standard solid phase peptide synthesis using standard protecting groups provided that the phosphine moiety on the amino acid is protected by a sulfide group bound thereto. Thus, a synthetic peptide containing the novel phosphine-containing amino acids can be prepared. Furthermore, a novel phosphine-containing amino acid can be introduced into a known peptide sequence at a selected location. When a synthetic peptide is prepared, the peptide can be of any selected length, and it is understood that conventional peptide synthesis permits the synthesis of peptides of approximately 40 amino acids in length. One could, of course, synthesize a selected peptide and incorporate it into a longer peptide by linking the peptides together. In this manner, a peptide of the present invention of any length can be prepared and is preferably at least 4 amino acids in length and can be at least as long as 1000 amino acids. More preferably, a phosphine containing peptide of the present invention is between 4 and 500 amino acids in length, and most preferably between 4 and 60 amino acids in length. After the peptide has been synthesized, it is cleaved from the polymeric resin associated with the solid phase synthesis apparatus and is purified by reverse phase HPLC or by other suitable methods known to those in the art.

The phosphine amino acids in the peptide are positioned in the peptide in a relationship that permits a transition metal to bind between two phosphine moieties of the phosphine amino acids. The spatial relationship of the phosphine amino acids will, therefore, depend on the particular secondary and tertiary structure of the peptide. The only requirement is that the two phosphine ligands be sufficiently near enough to each other when the peptide is in its folded configuration to bind a metal therebetween. The various secondary structures that a peptide can fold into are well known and include the s-helix, the B-pleated sheet, B-turns, as well as cyclic peptides. The tertiary structure of a peptide will also affect the spatial relationship of amino acid residues that are far apart in the linear sequence and the phosphine amino acids can be placed in the peptide to take advantage of the tertiary structure of a peptide that brings two distantly related amino acid residues spatially near each other enabling the binding of a metal therebetween. As an example, in a peptide that has the secondary structure of an α-helix, the phosphine containing amino acids in the peptide can be separated by between 0, 2, or 3 amino acids to position a metal between these amino acids. In one preferred embodiment, the phosphine amino acids are separated by 3 amino acids, which corresponds roughly to the standard 3.6 amino acid residues per turn of an α-helix which would place the phosphine containing amino acids spatially near each other in the three-dimensional structure of the peptide. Thus, by selecting the amino acids that surround the phosphine amino acids in the peptide, the secondary structure of the peptide and the environment of the metal bound to the phosphine moieties can be influenced.

It is well known that phosphine ligands can bind Group VIA through Group IB transition metals, such as Rhodium, Technetium, Ruthenium, Rhenium, Platinum, Nickel and the like. When a phosphine containing peptide is prepared in accordance with this invention, any of these transition metals can be bound between the two phosphine groups in the peptide. This provides a phosphine peptide-metal complex that can be used as a catalyst for inducing a stereoselective product of a chemical reaction or as a means for delivering such metal to a selected biological site. In particular, phosphines are known to bind to Technetium which has been shown to be particularly useful as a medical imaging diagnostic agent. By providing a phosphine-containing peptide capable of binding a metal useful in medical imaging or nuclear medicine, particular peptides can be engineered that have selected properties such as solubility, lipophilicity, bioavailability and selectivity that will permit unique and specific uses of the peptide as a metal delivery vehicle in a biological system.

The following Examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. It is further understood that the phosphine containing amino acids of this invention and as exemplified below may include various protecting groups to protect the amino, carboxyl, phosphine, or other functionalities of the amino acid which can be removed by methods known to these skilled in the art.

EXAMPLE 1

This example is provided to illustrate the synthesis of a phosphine containing amino acid in accordance with one aspect of the invention.

A phosphine sulfide amino acid, diphenylphosphinoserine sulfide, having the structure I as shown below was prepared.

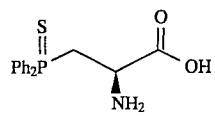

Figure 4:
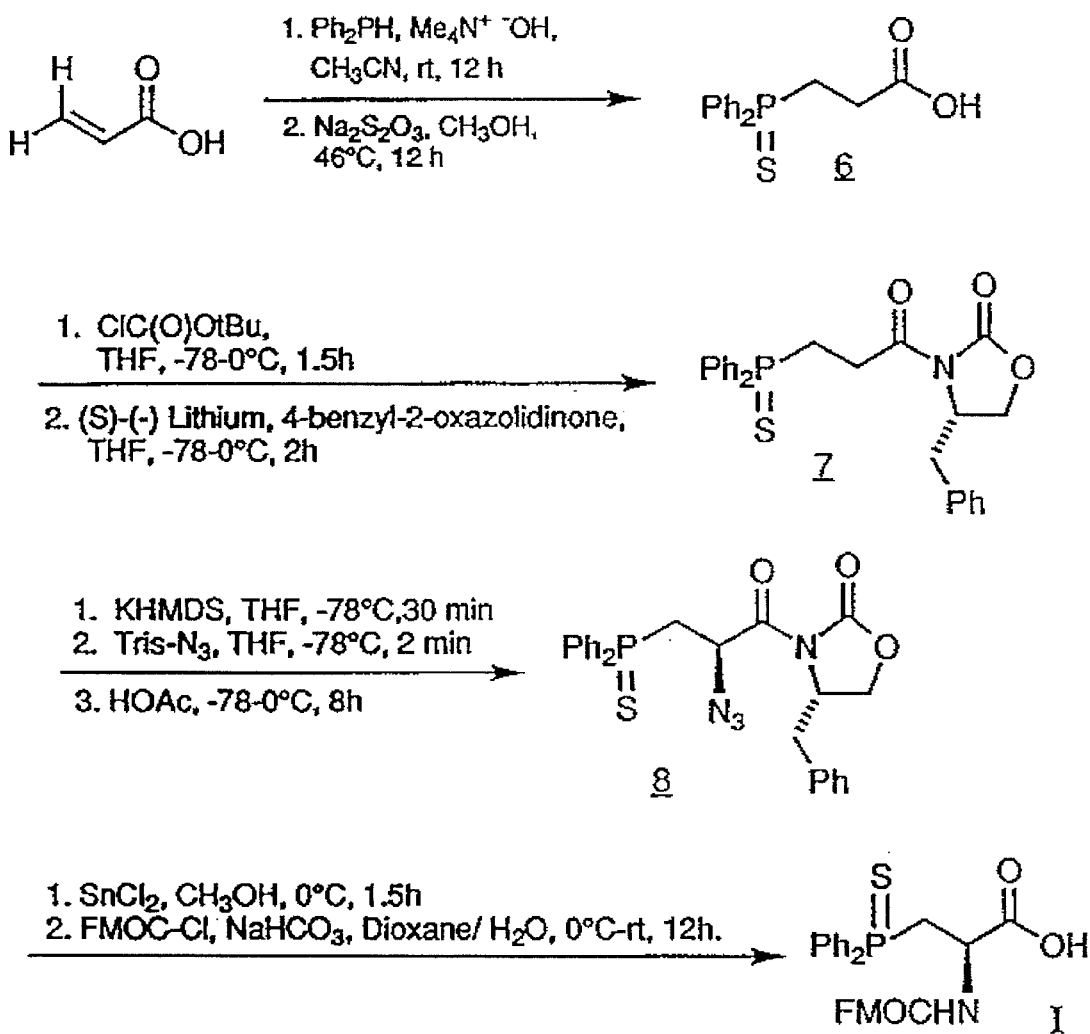
FIG. 4 is a schematic representation of the synthesis of the phosphine sulfide amino acid of structure I.

Generally, structure I is a derivative of serine and was synthesized as shown in FIG. 4 from acrylate by conjugate addition of diphenylphosphide anion to acrylate followed by conversion of the acid to the chiral oxazolidinone. Azide was added to the phosphine sulfide oxazolidinone by diastereoselective addition to the enolate of the oxazolidinone. Reduction of the azide to the amine, removal of the chiral auxiliary and protection of the amine yields the amino acid ready for peptide synthesis. The phosphine sulfide amino acid can be reacted with Raney nickel to reduce the phosphine sulfide to the phosphine.

More particularly, to a single neck roundbottom flask equipped with a magnetic stirbar was added 108 g (0.6 mol) of tetramethylammonium hydroxide and 1.2 liters of degassed $CH_3CN$. 52.2 ml (0.3 mol) of diphenylphosphine was then added via syringe. To the resulting solution, 20.6 ml (0.3 mol) of acrylic acid was added. The mixture was stirred at 21° C. for 12 hours. The $CH_3CN$ solution was then filtered into a 2 liter flask under $N_2$ and rinsed with 50 ml of $CH_3CN$. Sodium thiosulfate, $Na_3S_2O_3$, (237 g, 1.5 mol, 5 eq) was dissolved in 300 ml of degassed $H_2O$. The solution was then transferred under $N_2$ to the flask containing the phosphine acid of structure 6 in FIG. 4. The reaction was stirred at 46° C. for 12 hours. The reaction was worked up by removal of the $CH_3CN$ solvent on the rotovap. The solution, with some precipitate, was acidified to pH 3 using 2N HCl. The yellow slurry was then extracted with ethyl acetate. The ethyl acetate solution was washed with brine and dried ($MgSO_4$). After filtration, the solvent volume was reduced on a rotavapor. The product was dissolved in a minimum amount of hot ethyl acetate. Hexane was added to this solution. The heat was removed and the solution was allowed to cool to room temperature. Once crystals started to form, the flask was placed in a freezer (−20° C.) for further crystallization. Filtration of the crystals yielded 83.6 grams of structure 6 as shown in FIG. 4 (96%).

The conversion of the phosphine acid of structure 6 to the mixed anhydride was accomplished by the treatment of the acid (14.6 g., 50.3 mmol) with DIPEA (10.5 ml, 1.20 eq) and pivaloyl chloride (6.51 ml, 1.05 eq) in 300 ml THF at −78° C. The milky mixture was warmed to 0° C. over 60 minutes and was maintained at 0° C. for 30 minutes. The reaction mixture was filtered under $N_2$, and the filtrate was added to the lithium salt of the oxazolidinone at −78° C. The lithium salt of the oxazolidinone was prepared by the addition of 20.0 ml of 2.5 M nBuLi in hexane (1.0 eq) to the solution of oxazolidinone (8.9 g. 1.0 eq) in 10 ml of dry THF. Two 30 ml portions of THF were used to rinse in the remaining anhydride. The yellow solution was slowly warmed to 0° C. After which 100 ml of 0.5N HCl was added to quench the reaction. The product was worked up by removing THF on a rotovap. Ethyl acetate was added. The organic layer was washed with saturated $NaHCO_3$ solution, 1N HCl and brine and dried ($MgSO_4$). After filtration the solution was concentrated on a rotovap, and then warmed. A minimum amount of hexane was added to this solution. The solution was then allowed to come to room temperature for crystallization. Once crystals began to form, the flask was moved to a freezer for further crystallization. 18.4 g. of the oxazolidinone structure 7 as shown in FIG. 4 were isolated (84%).

Potassium hexamethyldisilazide (51.49 mmol, 1.25 eq 02.9 ml 0.5M in toluene) was added to 150 ml of dry THF at −78° C. under $N_2$. The oxazolidinone structure 7 as shown in FIG. 4 (18.50 g, 41.19 mmol) was dissolved in 150 ml of dry THF at −78° C. The resulting solution was slowly added (via cannula) to the KHMDS solution (in about 50 min.). Stirring was continued at −78° C. for 15 minutes before a precooled solution (−78° C.) of trisyl azide (15.91 g, 51.49 mmol, 1.25 eq) in 100 ml of THF was added. After 1 minute the reaction was quenched with 14 ml (6.0 eq) of glacial acetic acid. The cooling bath was removed, and the reaction was stirred at RT for 10 hours.

The reaction mixture was partitioned between $CH_2Cl_2$ (1000 ml) and dilute brine (1000 ml). The aqueous layer was washed with $CH_2Cl_2$ (x2). The organic phases were combined, washed with aqueous $NaHCO_3$, and dried ($MgSO_4$). After filtration the solvent was removed on the rotovap and then vacuum. The diastereomeric ratios of the resulting crude product of structure 8 of FIG. 4 was determined by $^{31}P$ NMR and found to be 32:1. The crude product was purified by silica gel chromatograph (35:65 ethyl acetate:hexane, Rf of the desired product is 0.25, Rf of the unwanted diastereomer is 0.034) yielding 16.2 g of the desired diastereomer yield 80.2%.

The α-azido carboximide structure 8 of FIG. 4 (4.12 g, 8.39 mmol) was dissolved in 90 ml of dry THF and cooled to 0° C. 402 mg (2.0 eq) of LiOH was dissolved in 30 ml of water, cooled to 0° C. These two solutions were then mixed and stirred for 15 minutes before 30 ml of 1N $NH_4Cl$ was added to the solution. THF was removed on a rotovap. The aqueous mixture was acidified to pH 3 using 1N HCl, and extracted with ethyl acetate. The ethyl acetate solution was washed with brine and dried ($MgSO_4$). The solvent was removed on a rotovap and the product dried invacuo. The material was purified by column chromatography (solvent: 35:65:1 ethyl acetate:hexane:HOAc).

The azido carboxylic acid was dissolved in MeOH(50 ml) and cooled to 0° C. $SnCl_2$ (2.2 eq) was dissolved in 30 ml of MeOH at 0° C., and was transferred to the azido acid solution via a syringe. The solution was warmed to room temperature in 60 minutes and was kept at room temperature for 1.5 hours. After removal of methanol, the sample was taken up in 50 ml of methylenechloride. After 2 hours in the freezer the solids were removed by filtration. After removal of $CH_2Cl_2$, the sample was dissolved in 80 ml of dioxane. This solution was cooled to 0° C. and $Na_2CO_3$ (2.67 g. 24.5 mmol, 6 eq) in 50 ml of water was added to the dioxane solution. FMOC-Cl (2.60 g. 1.2 eq) was added in small portions over 30 minutes. The resulting white solution was stirred at 0° C. for 4 hours and room temperature for 8 hours. After removal of dioxane the remaining aqueous mixture was acidified to pH 3 (2N HCl), and extracted with ethyl acetate. The organic layer was washed with brine and dried ($MgSO_4$). The crude product solidified in vacuo. The resulting phosphine sulfide amino acid having structure I (FMOC protected diphenylphosphinoserine was purified by silica gel chromatography (50:49:1 ethyl acetate: hexane: HOAc).

EXAMPLE 2

This example illustrates the synthesis of a phosphine sulfide containing amino acid from a cyclic amino acid having a secondary amino group. The phosphine sulfide amino acid, phenylphosphinoproline sulfide, has the structure II as shown below.

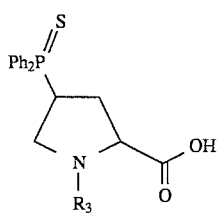

where $R_3$ is hydrogen or an amine protecting group, such as mesylate.

Figure 5:
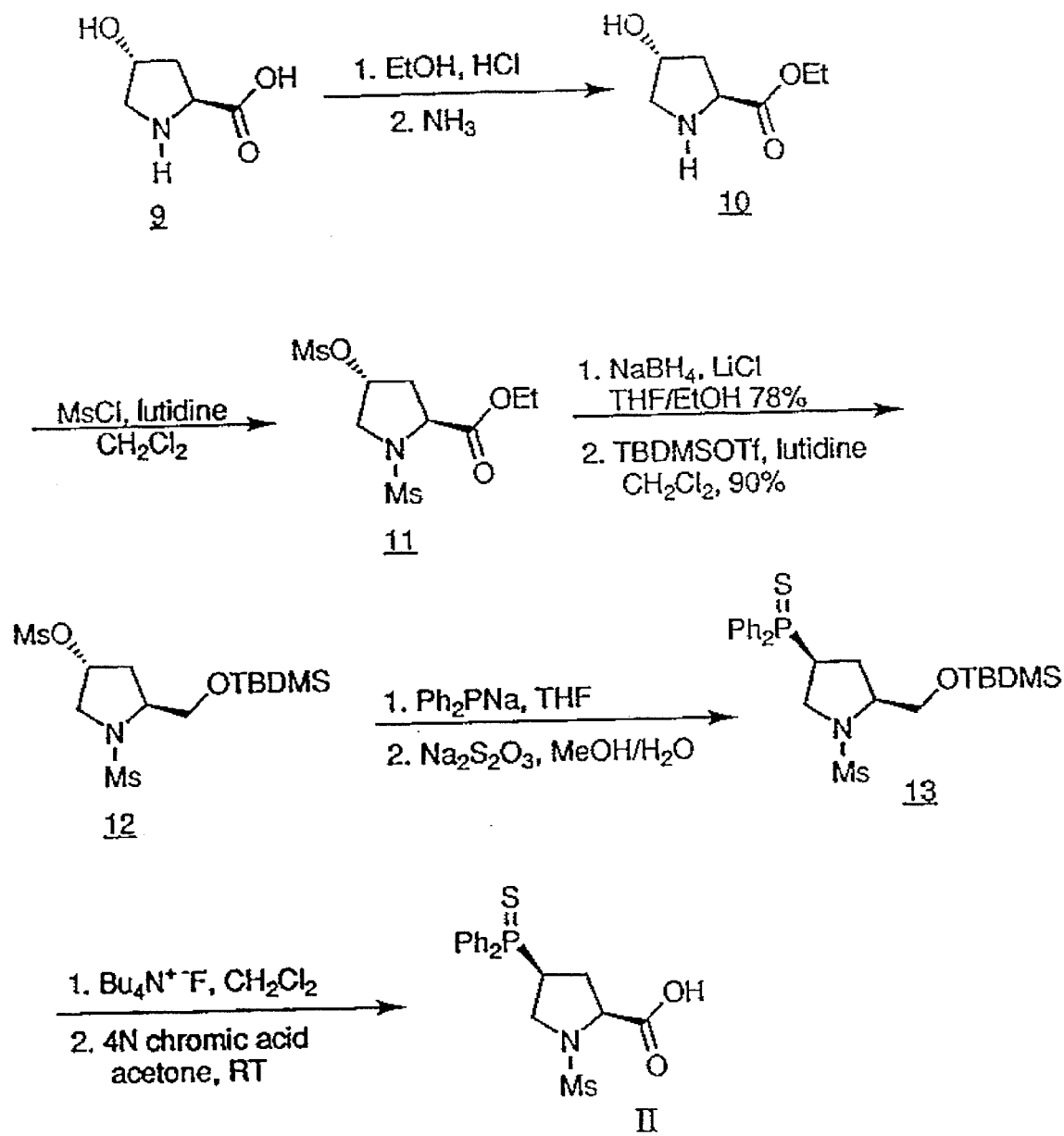
FIG. 5 is a schematic representation of the synthesis of the phosphine sulfide amino acid of structure II.

The phosphine amino acid of structure II was synthesized as schematically shown in FIG. 5 from hydroxyproline by reacting the hydroxyproline with hydrochloric acid and ethanol to produce the ethyl ester of hydroxyproline which was converted to the bis mesylate to activate the hydroxyl group and protect the amine group. The bismesylate ethyl ester of hydroxyproline was then reduced to the alcohol and protected as the t-butyldimethyl silyl ether. This compound was reacted with sodium diphenylphosphide to yield a phosphine which was reacted with sodium thiosulfate to convert it to the phosphine sulfide. Deprotection of the silylether and Jones oxidation yielded the phosphine sulfide amino acid which was converted to the phosphine sulfide containing amino acid of structure II. The phosphine sulfide amino acid having structure II can be incorporated into a peptide using standard solid phase peptide synthesis.

More particularly, hydrochloric acid was bubbled into a suspension of trans 4-hydroxy-L-proline (structure 9 of FIG. 5) (12 g, 91.5 mmoles) in ethanol (300 ml). After HCl had been bubbled through the mixture at room temperature for thirty minutes the mixture was cooled to 0° C. and HCl was bubbled through the solution for another thirty minutes. After HCl addition the mixture was stirred at 0° C. for four hours, followed by vacuum evaporation of ethanol to leave a white solid. The solid was placed under vacuum overnight to remove any remaining ethanol.

The hydrochloride salt was partially dissolved in 400 ml of chloroform and cooled to 0° C. in an ice-water bath. Ammonia was bubbled into the suspension for thirty minutes. At this point all precipitates were filtered away and the chloroform was vacuum evaporated, leaving the ethyl ester as a clear oil (13.9 g, 87.3 mmoles).

Trans 4-hydroxy-L-proline ethyl ester (structure 10 of FIG. 5) (13.9 g. 87.3 mmoles) was dissolved in 270 ml of dichloromethane and cooled to 0° C. in an ice-water bath. Triethylamine (26.78 ml, 192.1 mmoles) was added, followed by methanesulfonyl chloride (14.87 ml, 192.1 mmoles). The solution was stirred for six hours at 0° C. and placed in the freezer for two days. The crude mesylate solution was poured over 200 g of crushed ice and stirred until the ice melted. The organic layer was separated from the aqueous layer and washed with two 100 ml portions of water and one 100 ml portion of brine. After drying and evaporating with dichloromethane, the di-mesylate (structure 11 of FIG. 5) was obtained as a yellow oil (26 g. 82.6 mmoles).

Di-mesylate (26 g, 82.6 mmoles) and lithium chloride (7 g, 165 mmoles) were dissolved in a mixture of ethanol/tetrahydrofuran (1.5:1 v/v total volume: 1530 ml) and cooled to 0° C. in an ice-water bath. Sodium borohydride (6.25 g, 165 mmol) was added in portions, with vigorous bubbling resulting from each addition. The solution gradually changed to a white suspension ten minutes after the final addition of sodium borohydride. The suspension was removed from the ice-water bath and stirred overnight at room temperature. After 24 hours, 800 ml of water was added to quench the reaction and EtOH/THF was removed under vacuum. Two 700 ml portions of ethyl acetate were used to extract the aqueous layer. After drying (MgSO$_4$) and evaporating ethyl acetate, the di-mesylate hydroxyprolinol was obtained as a clear oil (16.82 g, 61.55 mmoles).

Di-mesylate hydroxyprolinol (16.82 g, 61.55 mmoles) was dissolved in 250 ml of dichloromethane. Lutidine (14.33 ml, 123 mmoles) was added and the resulting solution was cooled to 0° C. in an ice-water bath. TBDMSOTf (14.14 ml, 61.55 mmoles) was added and the solution was stirred for forty minutes. At the end of the reaction period, the solution was diluted to 400 ml with dichloromethane and washed with two 150 ml portions of water, three 100 ml portions of 1N citric acid, and one 100 ml portion of brine. The protected alcohol (structure 12 of FIG. 5) was obtained as a yellowish solid (22.78 g, 58.77 mmoles) after drying and removing the organic solvent.

A solution of diphenylphosphine in THF (5.59 ml, 32.14 mmoles of Ph$_2$PH in 15 ml of THF) was added dropwise to a solution of sodium amide (33.75 mmoles) in 50 ml of ammonia over a twenty minute period. Liquid ammonia was removed from the reaction by warming the dark orange solution to room temperature over a stream of nitrogen. When the solution had reached room temperature, mesylate (6.45 g, 16.65 mmoles in 15 ml of THF) was added dropwise to the anion over a twenty minute period.

After stirring for 24 hours, THF was evaporated from the brown phosphine mixture, leaving a muddy viscous liquid. The liquid was dissolved in 535 ml of degassed MeOH and a solution of sodium thiosulfate was added (26.33 g, 166.5 mmoles Na$_2$S$_2$O$_3$ in 535 ml of degassed water). Methanol was evaporated from the reaction mixture after stirring overnight at 45° C. The crude phosphine sulfide was extracted from the aqueous layer with two 250 ml portions of ethyl acetate. The ethyl acetate extracts were combined and washed with two 250 ml portions of water. After chromatography (80 CH$_2$Cl$_2$/20 hexane) the phosphine sulfide (structure 13 of FIG. 5) was isolated as a white solid (3.91 g, 7.66 mmoles). The phosphine sulfide product (5,641 g. 11.07 mmoles) was dissolved in 110 ml of THF and 22.14 of a 1M solution of tetrabutylammonium fluoride in THF was added. After one hour, the solution was evaporated to a total volume of 35 ml and poured into 300 ml of ethyl acetate. The organic layer was washed with three 150 ml portions of water, dried MgSO$_4$, and evaporated under vacuum to leave a yellowish semi-solid. After chromatography (60 EtOAc/40 hexane) the free alcohol was obtained as a white solid (3.98 g, 10 mmoles).

The free alcohol product (1.48 g, 3.74 mmoles) was dissolved in 90 ml of acetone and 4.5 ml of a 4N solution of chromic acid was added. The solution was initially orange, but changed to a greenish yellow solution with a green precipitate over thirty minutes. After two hours at room temperature, 15 ml of methanol was added to quench the reaction. The resulting mixture was filtered through a plug of celite/silica gel/celite using a medium pore size frit with ethyl acetate as the rinse solvent. The ethyl acetate rinse was discontinued when the filtered solution volume reached 400 ml. The ethyl acetate layer was washed with three 100 ml portions of water, dried with magnesium sulfate, and evaporated to leave the phosphine sulfide amino acid as a white solid (structure II of FIG. 5). $^{31}$P NMR indicates that the phosphine containing amino acid is actually a mixture of the phosphine sulfide/phosphine oxide in a 4:1 ratio (1.05 g, 2.57 mmoles sulfide and 0.25 g, 0.64 mmoles oxide).

EXAMPLE 3

Figure 6:
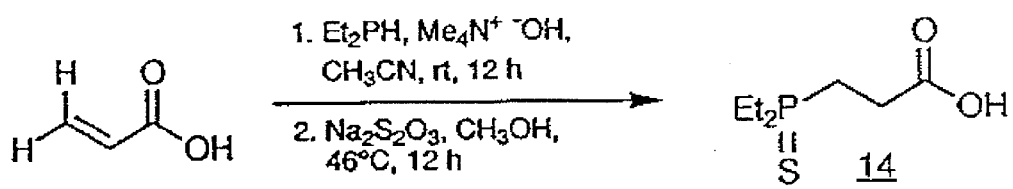
FIG. 6 is a schematic representation of the synthesis of the phosphine sulfide amino acid of structure V.
Figure 6:
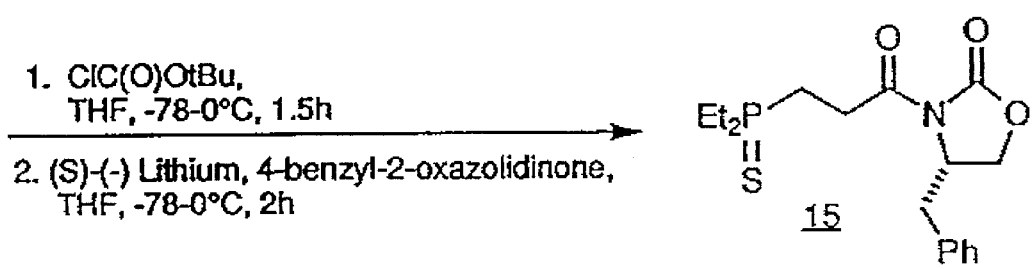
Figure 6:
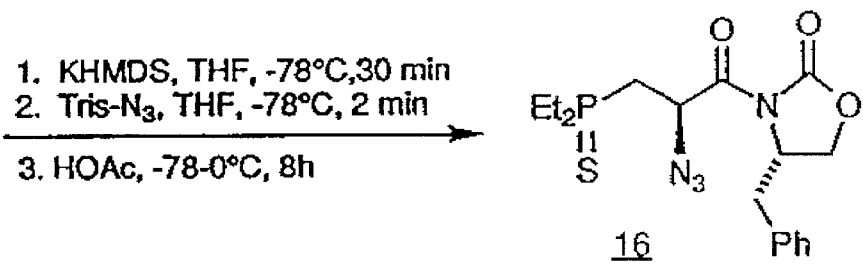
Figure 6:
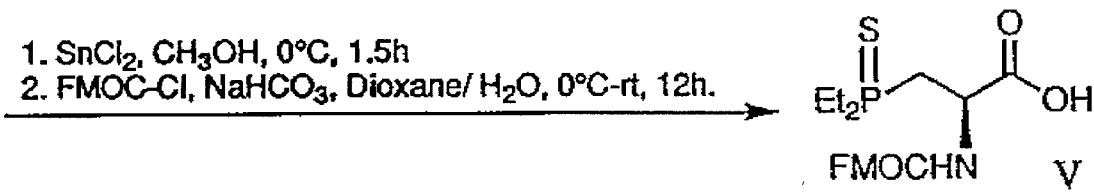

This example illustrates the synthesis of a phoshpine-containing hydroxyproline amino acid derivative where diethylphosphine anion is added by Michael addition to acrylate. The resulting FMOC protected phosphine containing amino acid has the structure V as shown below:

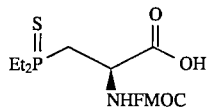

and the steps in the synthesis of an amino acid having structure V is summarized in FIG. 6. The amino acid of structure V is generally prepared using the same synthesis approach as used for the synthesis of the phosphine amino acid having structure I as shown in Example 1 except for the use of diethylphosphine in place of diphenylphosphine.

EXAMPLE 4

Figure 7:
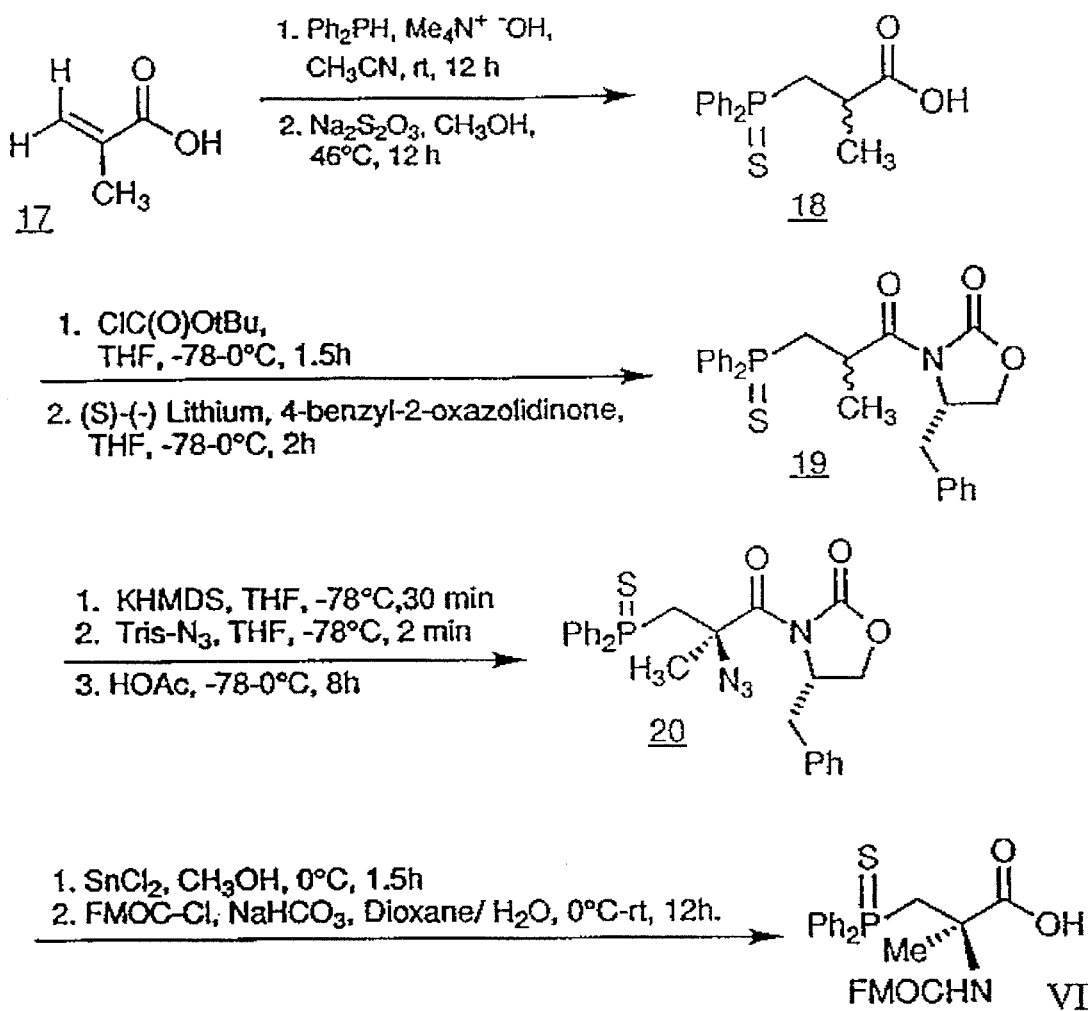
FIG. 7 is a schematic representation of the synthesis of the phosphine sulfide amino acid of structure VI.

This example illustrates a method by which a phosphine-containing α-methylated amino acid can be synthesized. The α-methylated phosphine amino acid would have the structure VI as shown below:

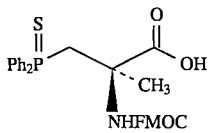

and a method for its synthesis is summarized in FIG. 7. The amino acid of structure VI would be prepared using the same synthesis approach as used for the synthesis of the phosphine amine acid having structure I as shown in Example 1 except that an α-methylated amine acid would be used as the starting material.

EXAMPLE 5

Figure 8:
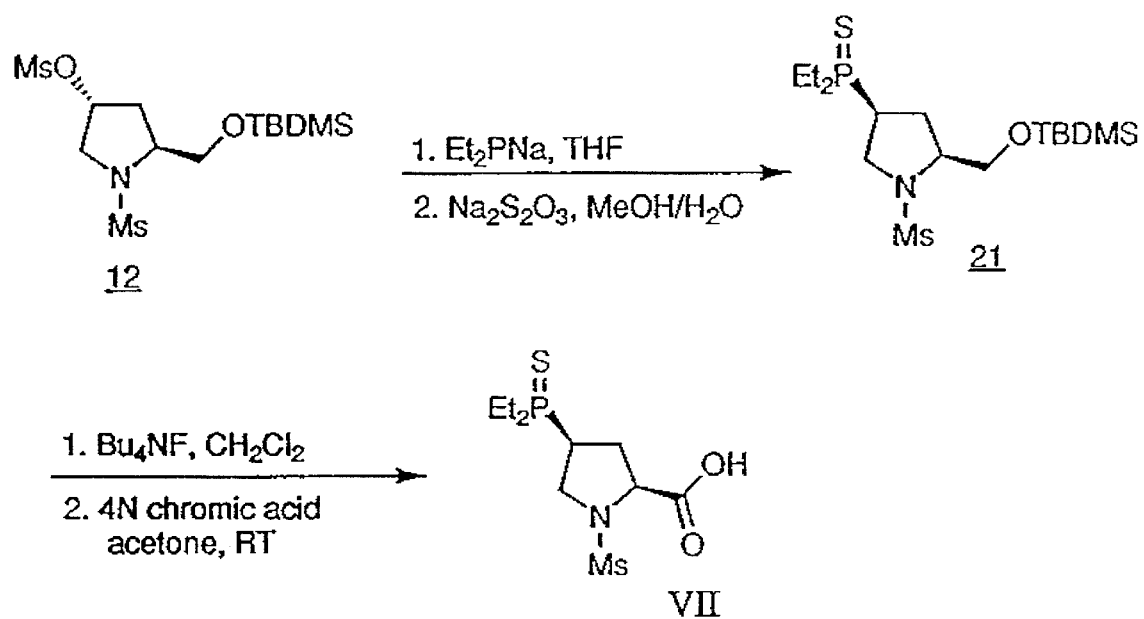
FIG. 8 is a schematic representation of the synthesis of the phosphine sulfide amino acid of structure VII.

This example illustrates a method by which a diethylphosphine derivated of the diphenylphosphine amine acid described in Example 2 can be synthesized. The resulting diethylphosphine amine acid would have the structure VII as shown below:

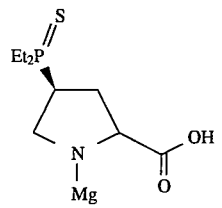

and a method for its synthesis is summarized in FIG. 8. This diethylphosphine amine acid would be synthesized as described in Example 2 with the substitution of the diethylphosphide anion for the diphenylphosphide anion.

EXAMPLE 6

Figure 9:
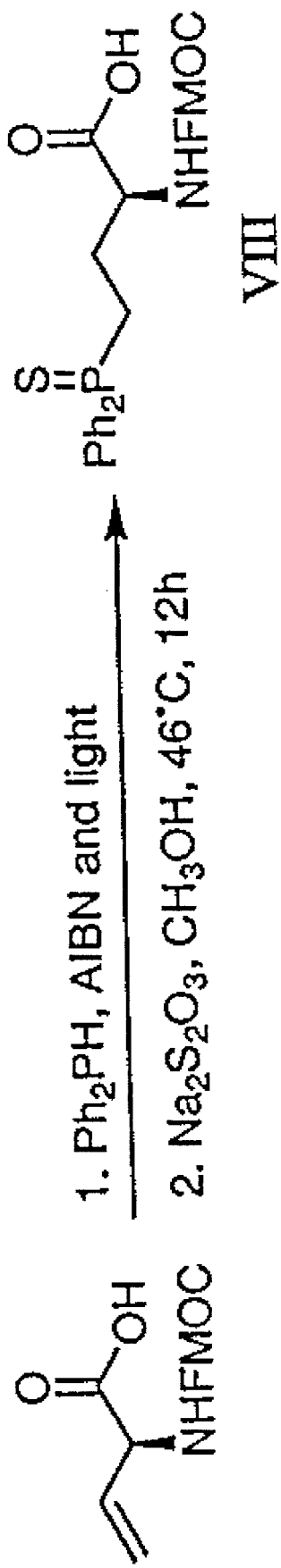
FIG. 9 is a schematic representation of the synthesis of the phosphine sulfide amino acid of structure VIII.

This example illustrates a method by which another phosphine-containing amine acid can be synthesized. The resulting phosphine-containing amine acid would have the structure VIII as shown below:

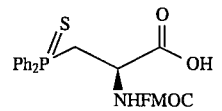

and a method for its synthesis is summarized in FIG. 9. The amine acid diphenylphosphine 2-aminoisobutyric acid of structure VIII would be synthesized by reaction of FMOC protected 2-aminoisobutyric acid with diphenylphosphine and light, followed by treatment with sodium thiosulfate, and methanol for 12 hours at 41° C. to yield the amino acid of structure VIII.

EXAMPLE 7

This example illustrates the incorporation of diphenylphosphinoserine as described in Example 1 into two peptide sequences. The resulting peptides have the sequences as shown below as structures III and IV: Ala-$Xaa_1$-Ala-Ala-$Xaa_2$-$Xaa_3$-Ala-Ala-$Xaa_4$-Ala-$Xaa_5$-Ala where Xaa is 2-aminoisobutyric acid, $Xaa_2$ is diphenylphosphinoserine, $Xaa_3$ is 2-aminoisobutyric acid, $Xaa_4$ diphenylphosphinoserine, and $Xaa_5$ 2-aminoisobutyric acid III (SEQ ID NO. 1); Ala-$Xaa_1$-Ala-Ala-$Xaa_2$-Val-Ala-Ala-$Xaa_3$-Ala-$Xaa_4$-Ala where $Xaa_1$ is 2-aminoisobutyric acid, $Xaa_2$ is diphenylphosphinoserine, $Xaa_3$ diphenylphosphinoserine, and $Xaa_4$ 2-aminoisobutyric acid IV (SEQ ID NO. 2).

These peptides were prepared synthetically by solid phase peptide techniques using FMOC protection of the amino end of the amino acid on a polystyrene resin. The peptide is purified by reverse phase HPLC. The phosphine sulfide derivative of diphenylphosphinoserine was used in the synthesis of the peptide to protect the phosphine moiety. The phosphine sulfide amino acid was incorporated as a dimer with alanine. This permitted the determination of optical purity of the synthetic phosphine sulfide amino acid and the dimer is easily purified by recrystallization. Treatment of the peptide containing the phosphine sulfides with Raney nickel overnight in methanol converts the phosphine sulfides to the free phosphines.

In particular, 300 mg of Raney nickel was weighed into a 5 ml vial, 2 ml of MeOH was added and the liquid was removed by a pipette. This washing process was repeated three times. Two ml of MeOH was then used to transfer the Raney Ni into a 25 ml Schlenk tube containing 20.0 mg of peptide IV (SEQ ID NO. 2) (14.3 mmol). The mixture was degassed by pump freeze thaw method (x3) and sealed. The reaction was heated at 48° C. with stirring for 18 hours. After cooling to room temperature, the reaction mixture was filtered under $N_2$ into a 10 ml two neck round bottom flask through a fritted filter funnel (fritt pore size was 10–15 Microns).

Figure 3:
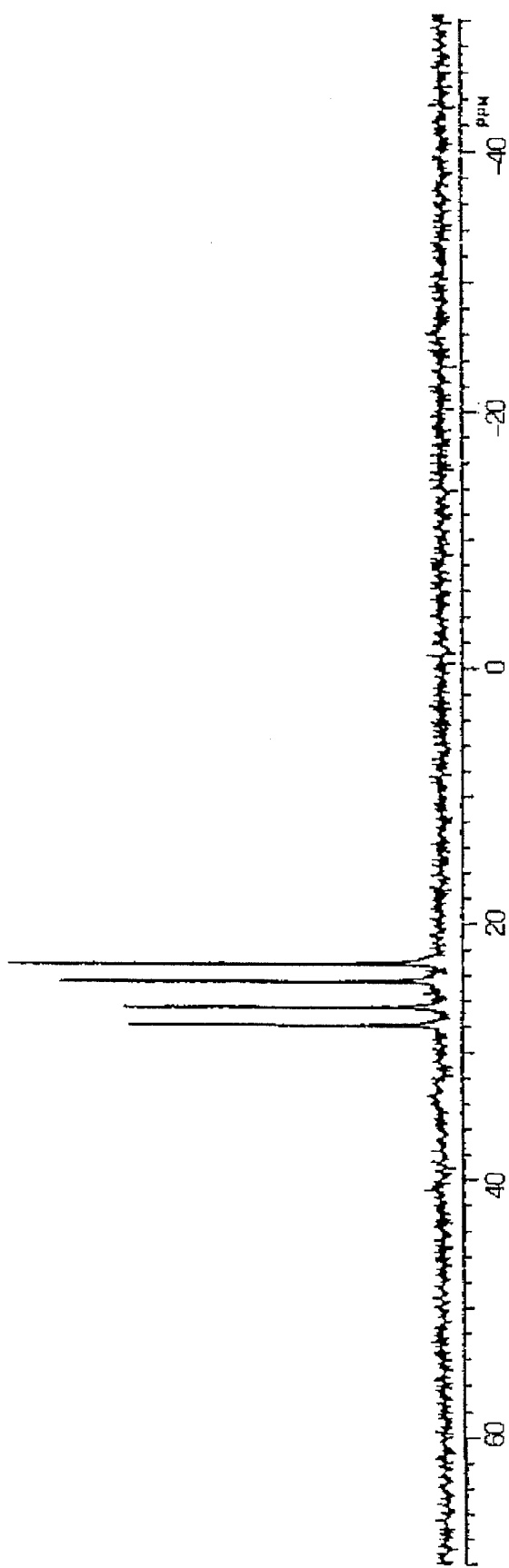
FIG. 3 is the $^{31}$P NMR spectra of the phosphine-containing peptide of SEQ ID NO. 1 after treatment with RhCl(NBD)$^+$BF$_4$.

The resulting peptide of structure III (SEQ ID NO. 1) or IV (SEQ ID NO. 2) thus provided a bis phosphine ligand wherein the phosphine containing amino acids were positioned in an i, i+4 relationship in the peptide (three amino acids between the phosphine containing amino acids) which permitted the binding of one metal atom between them. Peptides having structure III (SEQ ID NO. 1) and IV (SEQ ID NO. 2) were metalated with rhodium by mixing the peptide with $RhCl(NBD)^+ClO_4^-$ to yield the cationic rhodium containing peptide. The rhodium binds to the two diphenylphosphinoserine amino acids in the peptide to yield a phosphine-containing peptide metal complex. In particular, 2.58 mg (0.4×14.3 mmol) of $[Rh(NBD)Cl]_2$ and 2.32 mg (0.8×14.3 mmol) of $AgClO_4$ were weighed into a 1 ml vial 0.30 ml of MeOH was added. After stirring for 20 minutes the AgCl was filtered off. The filtrate was added to the phosphine peptide. The resulting orange solution was stirred under $N_2$ for 10 min before being transferred to a 25 ml Schlenk tube. MeOH was removed under vacuo. $^{31}P$ NMR was taken (solvent: $CD_3OD$) at this stage. The reaction sequence is followed by $^{31}$P NMR as shown in FIG. 3. The two phosphine resonances of the phosphine metal complex are split by the 100% natural abundance spin ½ $^{103}$Rh.

EXAMPLE 8

This example illustrates the applicability of the phosphine containing peptide metal complex having structure IV (SEQ ID NO. 2) (with rhodium bound between the two diphenylphosphinoserine amino acids) as described in Example 7 as a viable catalyst for the hydroformylation of styrene.

Figure 10:
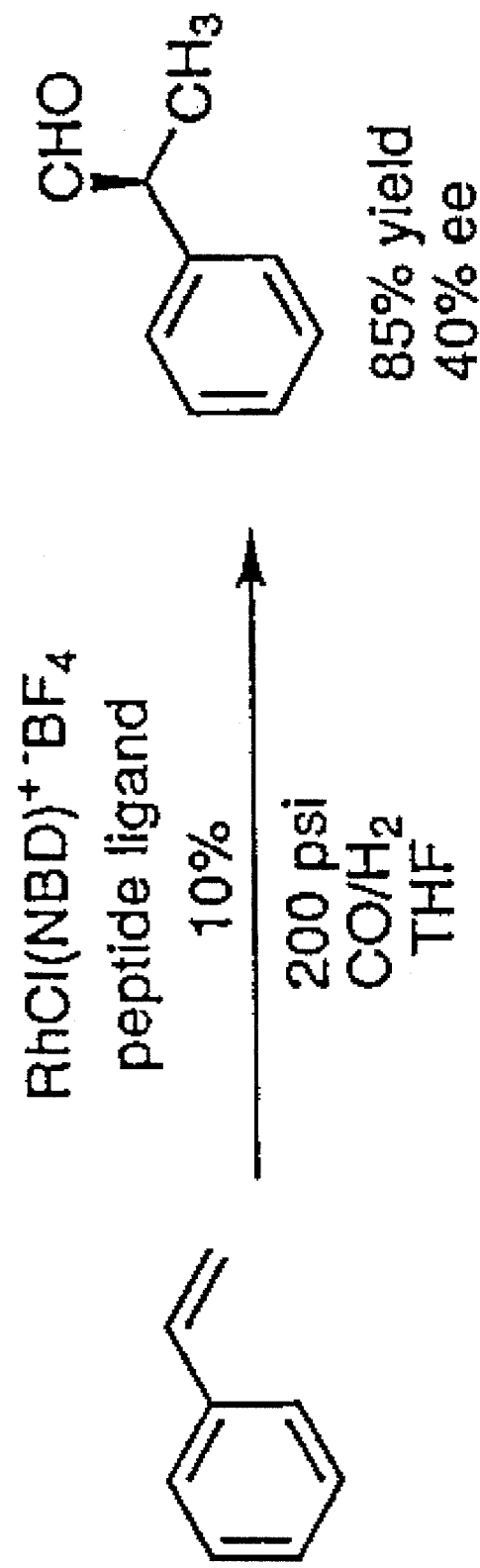
FIG. 10 is a schematic representation of the hydroformylation of styrene using the peptide having structure IV (SEQ ID NO. 2) as the catalyst.

The peptide IV (SEQ ID NO. 2) was prepared as described in Example 7 above. The hydroformylation reaction using this peptide as the catalyst is shown in FIG. 10. Two ml of THF was added to the schlenk flask containing the phosphine peptide. To this solution styrene (100 μl) was added. The reaction mixture was degassed by pump freeze thaw and the reaction vessel was then charged with 200 psi of CO/H$_2$ and stirred at room temperature. After 2 days the reaction was stopped and analyzed by chiral capillary gas chromatography. The yield of the branched aldehyde was 85% with a 40% enantiomeric excess.

---

What is claimed is:

1. A method of preparing a phosphine-containing peptide sequence, said method comprising the steps of:

providing a peptide sequence containing at least one amino acid having a phosphine sulfide moiety bonded to the side chain of said amino acid; and reacting said peptide sequence with a reducing agent to convert said phosphine sulfide moiety on said amino acid in said peptide sequence to a phosphine moiety to yield a phosphine-containing peptide sequence.

2. The method of claim 1 wherein said peptide sequence containing at least one amino acid having a phosphine sulfide moiety is prepared by solid phase peptide synthesis.

3. The method of claim 1 wherein at least two amino acids having a phosphine sulfide moiety are provided in said peptide sequence.

4. The method of claim 3 wherein said at least two amino acids having phosphine sulfide moiety are positioned in said peptide sequence such that said phosphine moieties in said phosphine-containing peptide sequence are sufficiently near each other when the phosphine-containing peptide sequence is in its folded configuration to bond a metal therebetween.

5. The method of claim 3 wherein said at least two amino acids having a phosphine moiety in said phosphine containing peptide sequence are separated on said phosphine containing peptide sequence by three non-phosphine containing amino acids.

6. The method of claim 1 wherein said reducing agent is Raney nickel and said reacting step is performed at between 38°–52° C. for an amount of time sufficient to convert said phosphine sulfide moieties on said amino acid to phosphine moieties.

7. A composition comprising an amino acid having a phosphine moiety bonded to the side chain of the amino acid.

8. The composition of claim 7 wherein said phosphine moiety is a phosphine sulfide.

9. A composition comprising a peptide containing at least one phosphine-containing amino acid.

10. The composition of claim 9 wherein said phosphine moiety on said at least one phosphine-containing amino acid is a phosphine sulfide.

11. The composition of claim 9 wherein said peptide contains at least two phosphine-containing amino acids.

12. The composition of claim 11 wherein said phosphine moiety on said at least two amino acids is a phosphine sulfide.

13. The composition of claim 12 wherein said at least two phosphine-containing amino acids are separated in said peptide by 0,2 or 3 non-phosphine containing amino acids.

14. The composition of claim 11 wherein said at least two phosphine-containing amino acids are positioned in said peptide in a manner positioning said phosphine-containing amino acids sufficiently near each other to bind a metal therebetween when said peptide is in its folded configuration.

15. A peptide having the amino acid sequence identified as SEQ ID NO. 1.

16. A peptide having the amino acid sequence identified as SEQ ID NO. 2.

17. The composition of claim 11 further comprising a metal selected from the group consisting of Group VIA––Group IB transition metals bonded between said at least two phosphine-containing amino acids.

18. The composition of claim 17 wherein said metal is selected from the group consisting of Rhodium, Technetium, Ruthenium, Rhenium, Platinum, and Nickel.

19. A peptide-metal complex comprising a peptide or mixture of peptides, each containing at least one phosphine containing amino acid and a transition metal bonded between two phosphine-containing amino acids.

20. A method for producing a chiral end product of a chemical reaction comprising utilizing an asymmetric phosphine-peptide metal complex as the catalyst for said reaction.

21. The method of claim 20 wherein said chemical reaction is selected from the group consisting of hydroformylation, hydrogenation, catalytic allylic alkylation, hydrosilation, hydrocyanation and hydrovinylation of olefins.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 12 amino acids
( B ) TYPE: amino acid
( D ) TOPOLOGY: linear ( i i ) MOLECULE TYPE: protein ( i i i ) HYPOTHETICAL: NO ( i x ) FEATURE:
( A ) NAME/KEY: Modified-site
( B ) LOCATION: 2
( D ) OTHER INFORMATION: /label=Aib
/ note="Modified and unusual amino acid is
2- Aminoisobutyric acid."

( i x ) FEATURE:
( A ) NAME/KEY: Modified-site
( B ) LOCATION: 5
( D ) OTHER INFORMATION: /label=Xaa
/ note="Modified amino acid is
Diphenylphosphinoserine."

( i x ) FEATURE:
( A ) NAME/KEY: Modified-site
( B ) LOCATION: 6
( D ) OTHER INFORMATION: /label=Aib
/ note="Modified and unusual amino acid is
2- Aminoisobutyric acid."

( i x ) FEATURE:
( A ) NAME/KEY: Modified-site
( B ) LOCATION: 9
( D ) OTHER INFORMATION: /label=Xaa
/ note="Modified amino acid is
Diphenylphosphinoserine."

( i x ) FEATURE:
( A ) NAME/KEY: Modified-site
( B ) LOCATION: 11
( D ) OTHER INFORMATION: /label=Aib
/ note="Modified and unusual amino acid is
2- Aminoisobutyric acid."

( x i ) SEQUENCE DESCRIPTION: SEQ ID NO:1:

Ala Xaa Ala Ala Xaa Xaa Ala Ala Xaa Ala Xaa Ala
1               5                   10

( 2 ) INFORMATION FOR SEQ ID NO:2:

( i ) SEQUENCE CHARACTERISTICS:
( A ) LENGTH: 12 amino acids
( B ) TYPE: amino acid
( D ) TOPOLOGY: linear ( i i ) MOLECULE TYPE: protein ( i i i ) HYPOTHETICAL: NO ( i x ) FEATURE:
    ( A ) NAME/KEY: Modified-site
    ( B ) LOCATION: 2
    ( D ) OTHER INFORMATION: /label=Aib
        / note="Modified and unusual amino acid is
        2- Aminoisobutyric acid."

( i x ) FEATURE:
    ( A ) NAME/KEY: Modified-site
    ( B ) LOCATION: 5
    ( D ) OTHER INFORMATION: /label=Xaa
        / note="Modified amino acid is
        Diphenylphosphinoserine."

( i x ) FEATURE:
    ( A ) NAME/KEY: Modified-site
    ( B ) LOCATION: 9
    ( D ) OTHER INFORMATION: /label=Xaa
        / note="Modified amino acid is
        Diphenylphosphinoserine."

( i x ) FEATURE:
    ( A ) NAME/KEY: Modified-site
    ( B ) LOCATION: 11
    ( D ) OTHER INFORMATION: /label=Aib
        / note="Modified and unusual amino acid is
        2- Aminoisobutyric acid."

( x i ) SEQUENCE DESCRIPTION: SEQ ID NO:2:

Ala  Xaa  Ala  Ala  Xaa  Val  Ala  Ala  Xaa  Ala  Xaa  Ala
1              5                             10